(12) United States Patent
Harnett et al.

(10) Patent No.: US 7,067,480 B2
(45) Date of Patent: Jun. 27, 2006

(54) COMPOSITIONS AND METHODS OF USE FOR ANTI-INFLAMMATORY AGENTS

(75) Inventors: William Harnett, Glasgow (GB);
Margaret M. Harnett, Glasgow (GB);
Iain B. McInnes, Glasgow (GB)

(73) Assignees: University of Strathclyde, Glasgow (GB); The University Court of the University of Glasgow, Glasgow (GB)

( * ) Notice: Subject to any disclaimer, the term of this patent is extended or adjusted under 35 U.S.C. 154(b) by 0 days.

(21) Appl. No.: 10/490,197

(22) PCT Filed: Sep. 20, 2002

(86) PCT No.: PCT/GB02/04310

§ 371 (c)(1),
(2), (4) Date: Sep. 7, 2004

(87) PCT Pub. No.: WO03/024474

PCT Pub. Date: Mar. 27, 2003

(65) Prior Publication Data

US 2005/0032686 A1 Feb. 10, 2005

(30) Foreign Application Priority Data

Sep. 20, 2001 (GB) .................................. 0122731.3

(51) Int. Cl.
*A61K 38/16* (2006.01)
*A61K 38/00* (2006.01)
(52) U.S. Cl. .............................................. 514/8; 512/8
(58) Field of Classification Search .................. 514/12; 530/350
See application file for complete search history.

(56) References Cited

OTHER PUBLICATIONS

Laan et al., "Glucocorticosteroids in the management of rheumatoid arthritis", 1999, Rheumatology (Oxford), 38(1), 6-12.*
H.S. Goodridge et al.; *Modulation of Macrophage Cytokine Production by ES-62, a Secreted Product of the Filarial Nematode Acanthocheilonema viteae*; The Journal of Immunology; 2001; pp. 940-945; vol. 167 (XP-002243871).
W. Harnett et al.; *Modulation of the host immune system by phosphorylcholine-containing glycoproteins secreted by parasitic filarial nematodes*; Biochimica Et Biophysica Acta; 2001; pp. 7-15; vol. 1539 (XP-002243872).
M. Whelan et al.; *A Filarial Nematode-Secreted Product Signals Dendritic Cells to Acquire a Phenotype that Drives Development of Th2 Cells*; The Journal of Immunology; 2000; pp. 6453-6460; vol. 164 (XP-002243873).
W. Harnett et al.; *Immunomodulation by Filarial Nematode Phosphorylcholine-containing Glycoproteins*; Parasitic Nematodes; 2001; pp. 399-414; Cabi Publishing; Wallingford, UK (XP-001152690).
W. Harnett et al.; *Immunomodulatory properties of a phosphorylcholine-containing secreted filarial glycoprotein*; Parasite Immunology; 1999; pp. 601-608 (XP-002243874).
Copy of International Search Report for PCT/GB02/04310 completed Jun. 11, 2003.
Copy of International Preliminary Examination Report for PCT/GB02/04310 completed Dec. 9, 2003.
Haslam, S., et al., "Characterisation of the Phosphorylcholine-Containing N-Linked Oligosaccharides in the Excretory-Secretory 62 kDa Glycoprotein of *Acanthocheilonema viteae,*" *Molecular and Biochemical Parasitology*, 1997, pp. 53-66, vol. 85, Elsevier Science B.V.
Harnett, W., et al., "*Acanthocheilonema viteae*: Phosphorylcholine Is Attached to the Major Excretory-Secretory Product via an N-Linked Glycan," *Experimental Parasitology*, 1993, pp. 498-502, vol. 77, Academic Press, Inc.
Harnett, W., et al., "Molecular Cloning and Demonstration of an Aminopeptidase Activity in a Filarial Nematode Glycoprotein," *Molecular and Biochemical Parasitology*, 1999, pp. 11-23, vol. 104, Elsevier Science B.V.
Houston, K., and Harnett, W., "Prevention of Attachment of Phosphorylcholine to a Major Excretory-Secretory Product of *Acanthocheilonema viteae* Using Tunicamycin," *American Society of Parasitologists*, 1996, pp. 320-324, vol. 82(2).
Leung, B., et al., "Combined Effects of IL-12 and IL-18 on the Induction of Collagen-Induced Arthritis," *The Journal of Immunology*, 2000, pp. 6495-6502, The American Association of Immunologists.
Piedrafita, D., et al., "Protective Immune Responses Induced by Vaccination with an Expression Genomic Library of *Leishmania major,*" *The Journal of Immunology*, 1999, pp. 1467-1472, The American Association of Immunologists.

* cited by examiner

*Primary Examiner*—Jon Weber
*Assistant Examiner*—Suzanne M. Noakes
(74) *Attorney, Agent, or Firm*—Alston & Bird LLP

(57) ABSTRACT

This invention relates to the use of a phosphorylcholine-containing glycoprotein in the treatment or prophylaxis of diseases associated with inflammation. In particular, the present invention relates to the use of ES-62 for the treatment or prophylaxis of autoimmune diseases associated with abnormal inflammation, such as rheumatoid arthritis.

3 Claims, 13 Drawing Sheets

AAVLPEKTVAPKNYIQETFGKEVAELIQY
ITKGEEVGLAYQWLTKLVDGFGHPMVG
SDSLEKSIAFLEESLKNDNFDKVHTEEVP
NLPHWVRGNDVVEMIEPRNQRLNVLAI
GGSEPASATGEVTVIYDLDDVKPDDVR
GKIVVTAQTFAGYPLTLKYRRSVKLFEQ
LGAIGVLVKSITSFSINSPHTGTGAE<u>NTT</u>I
PAACLTIEEAEMLERLYRSGKKIVIRMDM
KSHYEEPI<u>NSS</u>NLIFEITGSERPSEVVLLSA
HVDSWDVGQGALDDGAGCAVVWSAL
HSLKKLAERNPKFKPKRTIRGIFWTSEEQ
GYGGAKHYYITHK<u>NDS</u>PEKFYFVSETDT
GTFKSTNWLAHLSFSGDKKSMLRLKEIT
RLLSRNGIALGLI<u>NSS</u>VQGDVTFWAKDG
IPSVNYIPDKAVDYYFYFHHTAGDYMTV
LKDGDLEYTTSIFATLHVIANMDDWGS
DPNQPQQLNSKQSTTEKSDRKKL

FIG. 1

Experimental Design

- ES-62 = 2µg/animal (s.c.) at d-2, d0 + d21
- *ES-62 as above & 3 extra daily treatment (d22-24) + 1/3 days until end of study;
- PBS as control

COMPOSITIONS AND METHODS OF USE FOR ANTI-INFLAMMATORY AGENTS

FIELD OF THE INVENTION

The present invention relates to the use of a glyco-protein for the treatment or prophylaxis of diseases associated with inflammation, in particular the present invention relates to the use of ES-62 for the treatment or prophylaxis of autoimmune diseases associated with abnormal inflammation, such as rheumatoid arthritis (RA).

BACKGROUND OF THE INVENTION

Filarial nematodes are arthropod-transmitted parasites of vertebrates including humans. Infection is long-term with individual worms surviving for in excess of five years. The consensus of opinion amongst workers in this field is that such longevity reflects suppression or modulation of the host immune system and indeed "defects" in immune responsiveness have been revealed in infected individuals. These defects incorporate impairment of lymphocyte proliferation and bias in production of both cytokines and antibodies. With respect to cytokines the bias can be shown in reduced production of the pro-inflammatory IFN-γ and increased production of the anti-inflammatory IL-10. For antibodies, there are imbalances in IgG subclasses—greatly elevated IgG4 (an antibody of little value in eliminating pathogens due to an inability to activate complement or bind with high affinity to phagocytic cells); decreases in other IgG subclasses. Overall therefore, the picture is of an immune response demonstrating a somewhat suppressed, anti-inflammatory phenotype which is often classified as "TH-2" ("TH" is derived from a category of T-lymphocyte referred to as "helper"). It has been speculated that such a phenotype is conducive to both parasite survival and host health, the latter by limiting pathology resulting from an over-aggressive immune response. Consistent with this, it is noteworthy that the majority of humans who harbour these parasites demonstrate little evidence of detrimental pathology.

Modulation of the host immune system is likely to involve the active participation of filarial nematodes and hence considerable effort has been spent in characterising the biological properties of molecules secreted by the worms.

Goodridge et al. in the Journal of Immunology, 2001, 167, discuss modulation of macrophage cytokine production by ES-62 resulting in suppression of the production of pro-inflammatory cytokines which may contribute to the immunomodulatory properties of ES-62 that drive the generation of immune responses with an anti-inflammatory and/or TH-2 phenotype. Although this article provides a rationale for the changes seen in the immune response, no guidance is provided on whether ES-62 may be useful in the clinic for preventing or treating any particular disease(s), in particular those diseases involving inflammation.

Harnett and Harnett in Biochemica et Biophysica Acta, 1539, (2001), 7–15 report investigations into the underlying mechanism of action of ES-62 and phosphorylcholine (PC). It is concluded that PC has various actions, including a number of immunomodulatory properties.

The prior art, at best, may only suggest that ES-62 has a role in the mediation of diseases involving an inflammatory response due to the effect of ES-62 on production of inflammatory cytokines. However, these investigations have been performed only in vitro, and no evidence is presented to show that ES-62 may be used to treat disorders associated with inflammation.

Evidence of such molecules having a clinical use has hitherto not been demonstrated, and thus an object of the present invention is to obviate and/or mitigate the current treatment inadequacies of diseases associated with inflammation.

SUMMARY OF THE INVENTION

Broadly speaking the inventors have been generally investigating the ES-62 molecule which appears to have an immunomodulatory effect.

According to a first aspect of the present invention there is provided the compound ES-62 or physiologically active derivatives for use as a medicament.

The medicament may be used in the in vivo treatment or prophylaxis of inflammatory diseases in an animal. The animal requiring treatment or prophylaxis is usually a human or non-human mammal.

According to a second aspect of the present invention, there is provided the compound ES-62 or physiologically active derivatives thereof for use in treatment or prophylaxis of inflammatory diseases in an animal.

The animal requiring treatment or prophylaxis is usually a human or non-human mammal.

Many diseases involve inflammation, and particularly relevant diseases for treatment or prophylaxis according to the present invention are autoimmune diseases such as type 1 diabetes melitus, rheumatoid arthritis, psoriasis, multiple sclerosis, autoimmune hepatitis, sarcoidosis, inflammatory bowel disease, and chronic obstructive pulmonary disease.

The present invention has particular application for the treatment or prophylaxis of rheumatoid arthritis.

According to a third aspect of the present invention there is provided the use of ES-62 for the manufacture of a medicament for the treatment or prophylaxis of inflammatory disease. In a fourth aspect of the present invention there is provided a method for the treatment or prophylaxis of inflammatory disease in an animal comprising administering to said animal a therapeutically or prophylactically effective amount of ES-62 or physiologically functional derivative thereof.

Preferably, ES-62 is used therapeutically to treat inflammatory disease.

BRIEF DESCRIPTION OF THE DRAWINGS

FIG. 1 shows the amino acid sequence of ES-62 where potential N-linked glycosylation sites are under-lined. Potential N-linked glycosylation sites are underlined. It is currently unknown as to how many of these are utilized and of the utilized ones, how many have linkage with phosphorycholine-containing glycans.

FIG. 2 also shows that the phosphorycholine is bound to the glycan and not the protein.

FIG. 4 shows graphs indicating the development of arthritis with time.

PBS (n=13), ES-62 (n=12), ES-62 Multi (n=14). †p<0.05 PBS vs. ES-62, *p<0.05 PBS vs. ES-62 Multi, Mann-Whitney U-test.

FIG. 5 shows suppression of antigen-induced cell proliferation and pro-inflammatory cytokine production in lymph node cultures at day 33. FIG. 5A. Thymidine uptake ($\times 10^3$ cpm) for collagen-treatment vs. controls in PBS, ES-62, and ES-62 Multi conditions. FIG. 5B. IFN-γ (pg/ml) for collagen-treatment vs. controls in PBS, ES-62, and ES-62 Multi conditions. FIG. 5C. TNF-α(pg/ml) for collagen-treatment vs. controls in PBS, ES-62, and ES-62 Multi conditions. FIG. 5D. IL-6 (pg/ml) for collagen-treatment vs. controls in PBS, ES-62, and ES-62 Multi conditions. FIG. 5E. IL-10 (pg/ml) for collagen-treatment vs. controls in PBS, ES-62, and ES-62 Multi conditions. Data are expressed as mean +/−S.D., *p<0.05.

FIG. 6 shows that ES-62 treatment maintains the inhibition of both cell proliferation and inflammatory cytokine production at day 50. FIG. 6A. Thymidine uptake ($\times 10^3$ cpm) for collagen-treatment vs. controls in PBS, ES-62, and ES-62 Multi conditions. FIG. 6B. IFN-γ (pg/ml) for collagen-treatment vs. controls in PBS, ES-62, and ES-62 Multi conditions. FIG. 6C. TNF-α (pg/ml) for collagen-treatment vs. controls in PBS, ES-62, and ES-62 Multi conditions. FIG. 6D. IL-6 (pg/ml) for collagen-treatment vs. controls in PBS, ES-62, and ES-62 Multi conditions. Data are expressed as mean +/−S.D., *p<0.05.

Figures 7A, 7B:
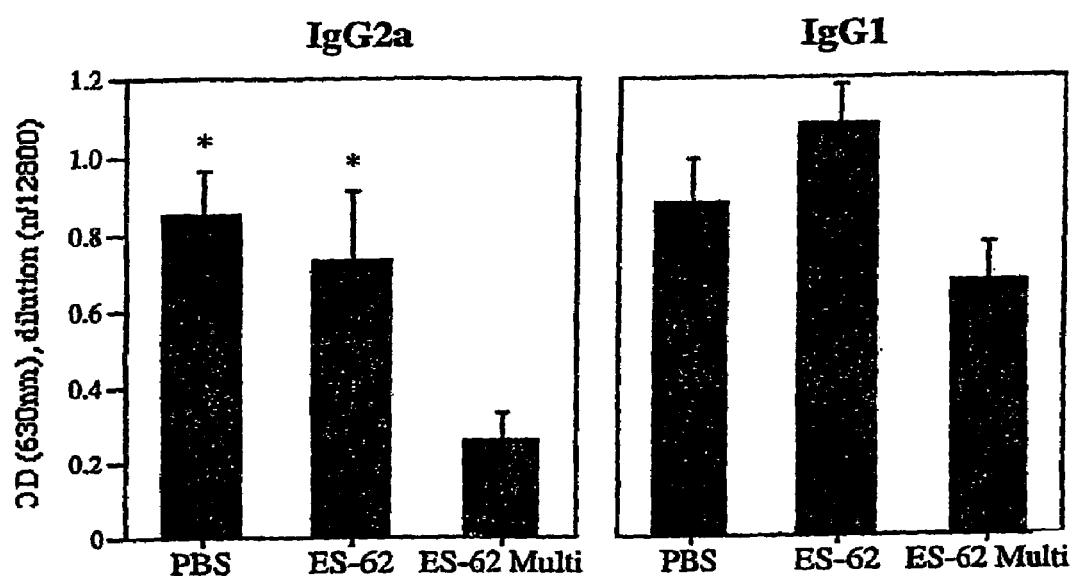

FIG. 7 shows a reduction in production of the TH-1 associated antibody, IG2a by ES-62 treatment at day 50. FIG. 7A. Detection levels of anti-collagen IgG2a in PBS, ES-62, and ES-62 Multi conditions. FIG. 7B. Detection levels of anti-collagen IgG1 in PBS, ES-62, and ES-62 Multi conditions. Pooled data of individual measurements (n=5/group) & expressed as mean +/−SEM; *p<0.05, Mann-Whitney test.

Figure 8A:
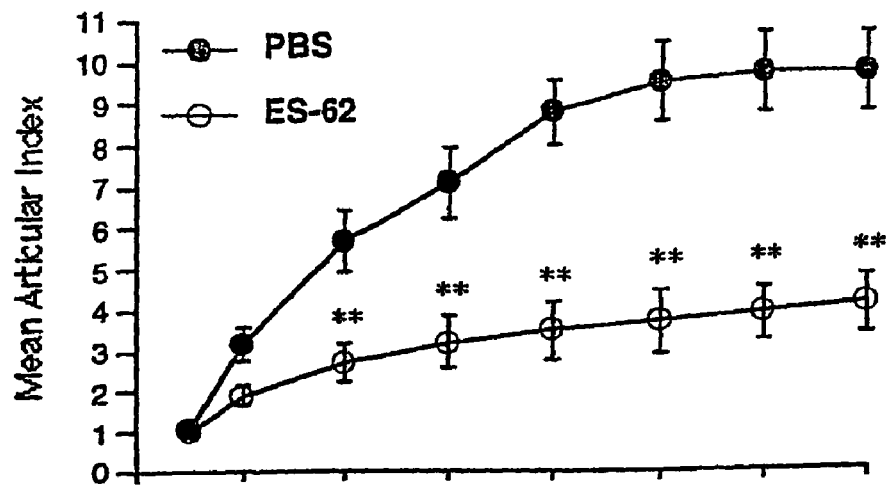
Figure 8B:
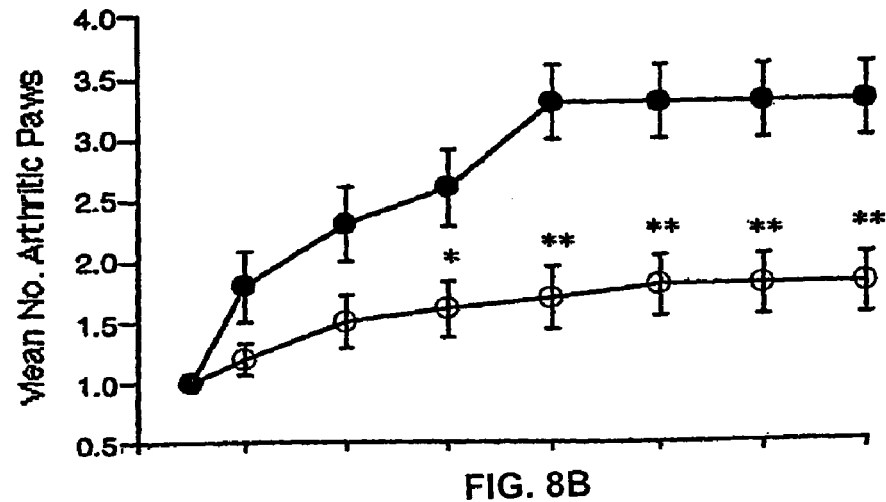
Figure 8C:
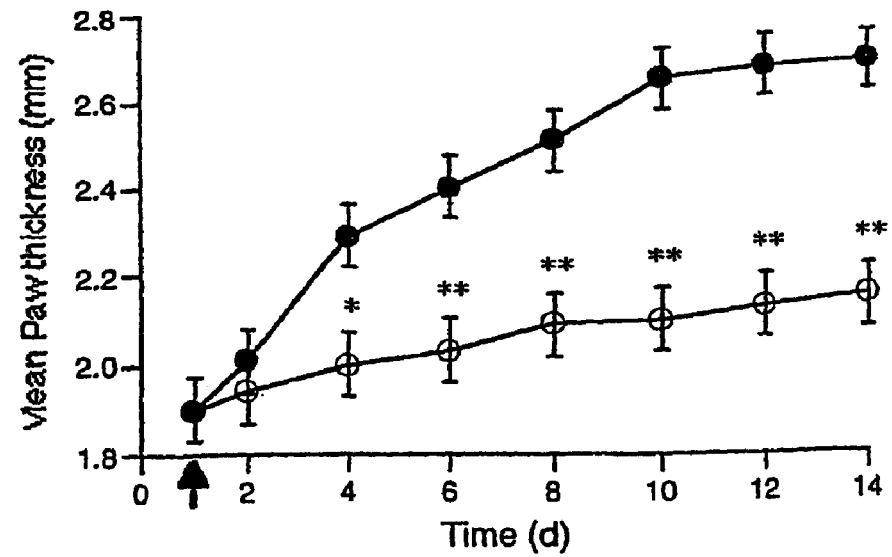
Figure 9A:
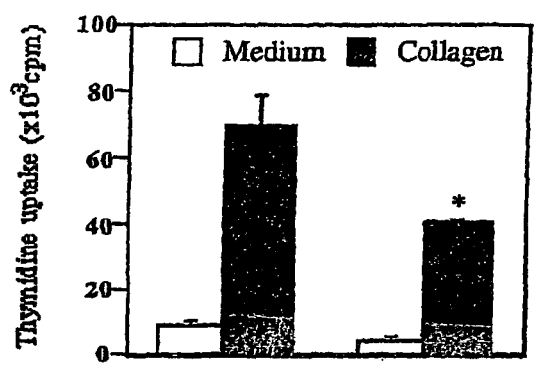
Figure 9B:
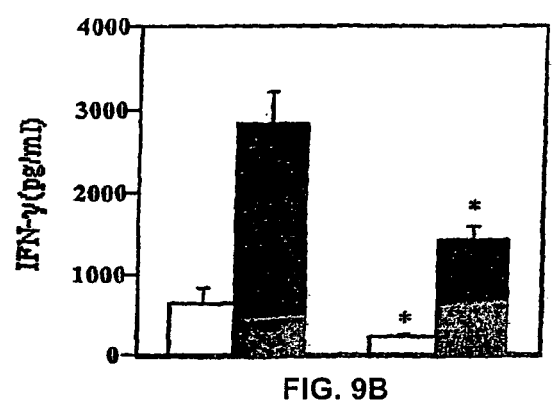
Figure 9C:
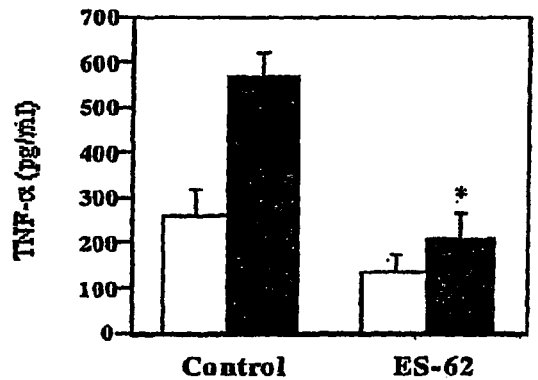
Figure 9D:
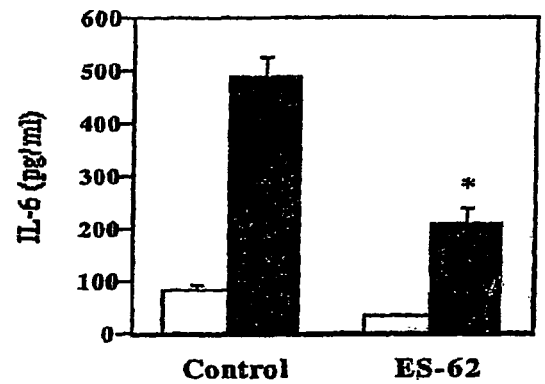

FIG. 8 shows ES-62 treatment is effective in preventing proaression of established arthritis. FIG. 8A. Mean articular index as a function of time. FIG. 8B. Mean number of arthritic paws as a function of time. FIG. 8C. Mean paw thickness (mm) as a function of time. Data are mean +/−SEM; PBS (n=10); ES-62 (sc 2 µg daily for 14 days, n=10). *p<0.05 **p<0.01 Mann-Whitney test.

FIG. 9 shows ex-vivo suppression of antigen-induced cell proliferation in lymph node cultures upon ES-62 administration and also suppression of production of certain pro-inflammatory cytokines in established collagen-induced arthritis. FIG. 9A. Thymidine uptake ($\times 10^3$ cpm) for collagen-treatment vs. controls in PBS and ES-62 conditions. FIG. 9B. IFN-γ (pg/ml for collagen-treatment vs. controls in PBS and ES-62 conditions. FIG. 9C. TNF-α (pg/ml) for collagen-treatment vs. controls in in PBS and ES-62 conditions. FIG. 9D. IL-6 (pg/ml) for collagen-treatment vs. controls in in PBS and ES-62 conditions. Data are expressed as mean +/−SEM (n=5/group, d15 ES-62), *p<0.05 Student's T-test.

Figures 10A, 10B:
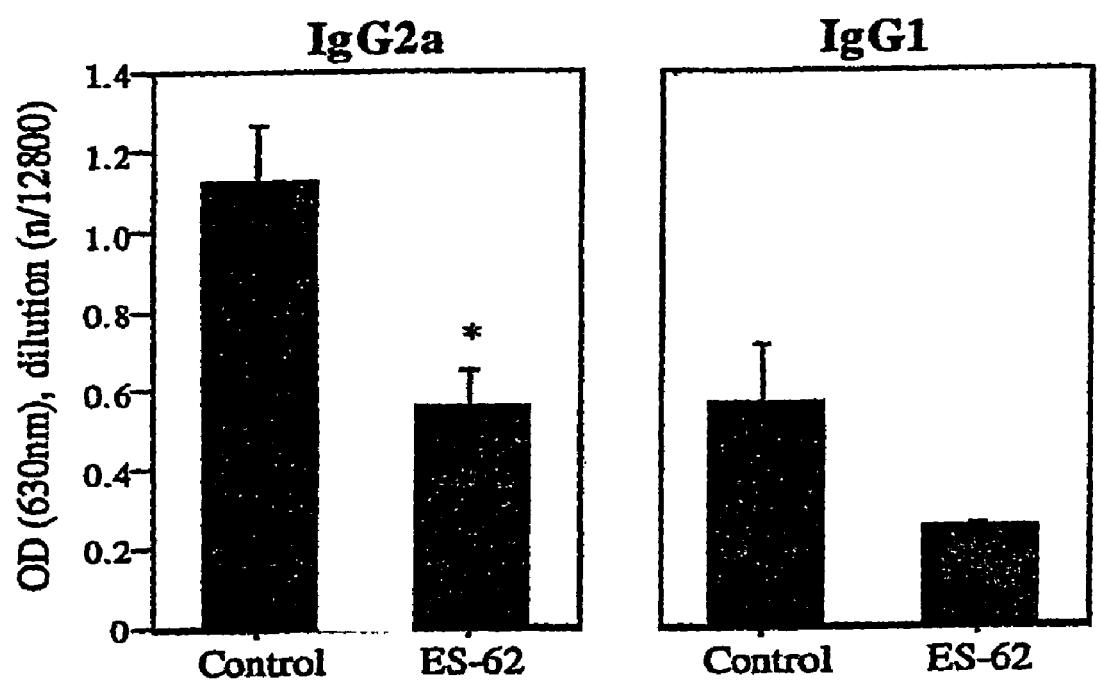

FIG. 10 shows a reduction in production of the TH-1 antibody. IgG2a upon administration of ES-62 in established collagen-induced arthritis. FIG. 10A. Detection levels of anti-collagen IgG2a. FIG. 10B. Detection levels of anti-collagen IgG1. Pooled data of individual measurements (n=5/group d15 ES-62) & expressed as mean +/−SEM: *p<0.05, ANOVA test.

Figure 11A:
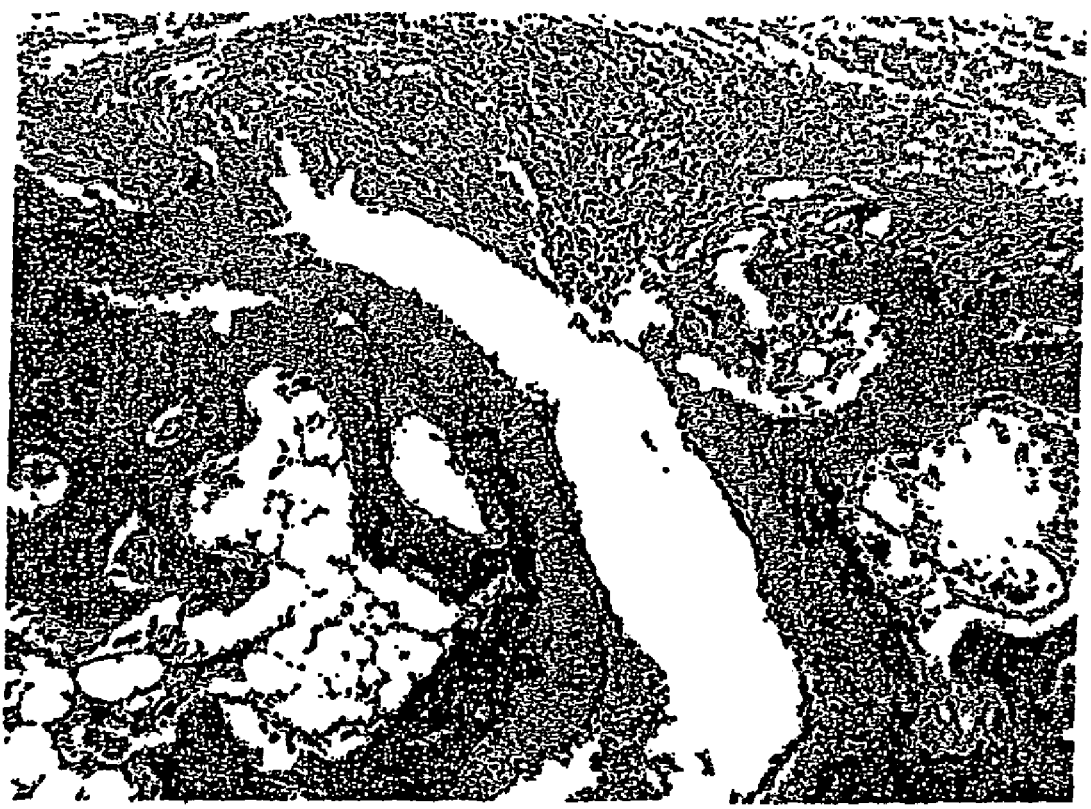
Figure 11B:
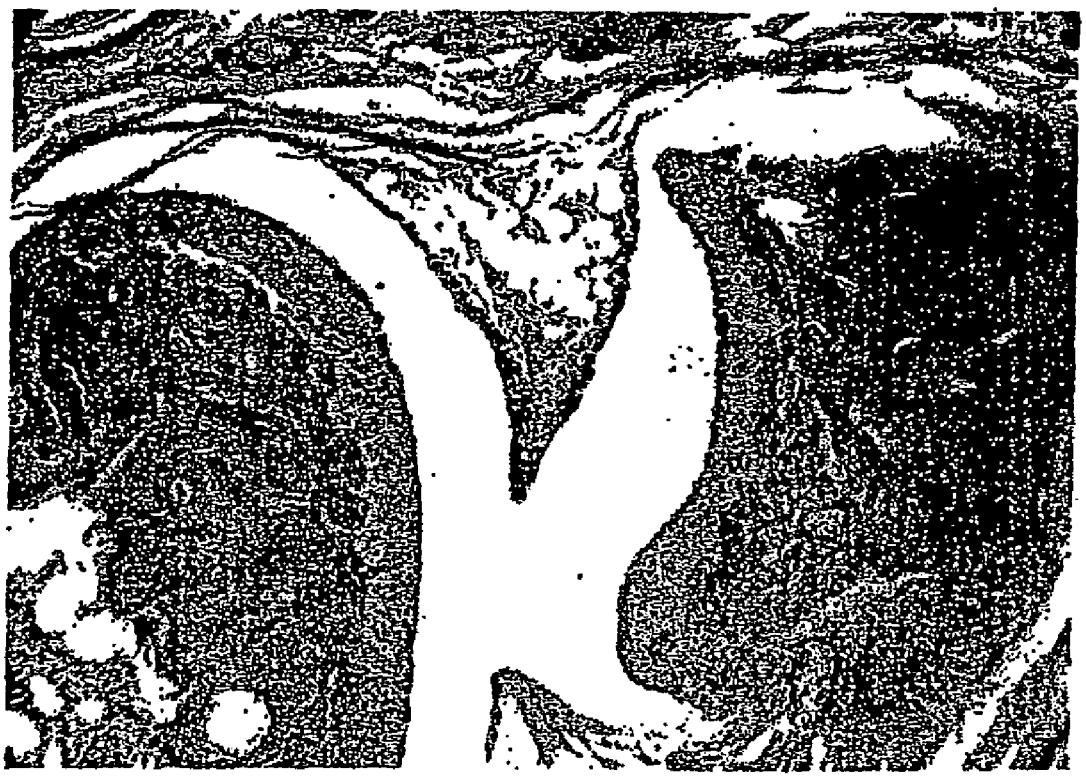

FIG. 11 shows sections of arthritic hind paws of mice stained with hematoxylin and eosin showing a prevention in cartilage surface erosion and inflammation in ES-62 treated mice. FIG. 11A. PBS-treated mice. FIG. 11B. ES-62-treated mice. Mice were treated with PBS (FIG. 11A) or ES-62 (FIG. 11B) according to the therapeutic protocol and arthritic hind paws were removed and stained with hematoxylin and eosin. Profound cartilage surface erosion and inflammation was observed in PBS controls.

Figure 12A:
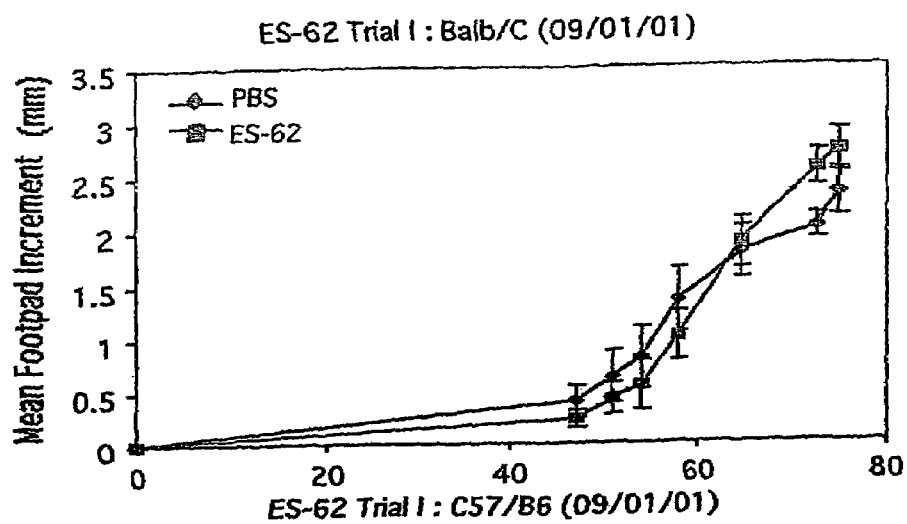
Figure 12B:
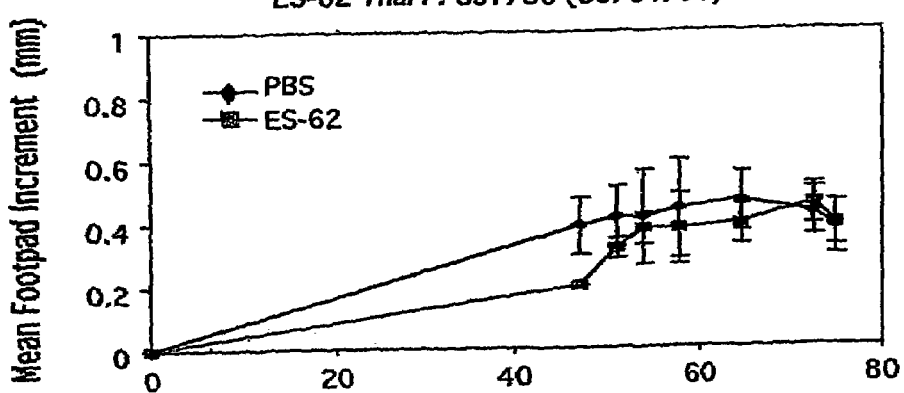
Figure 12C:
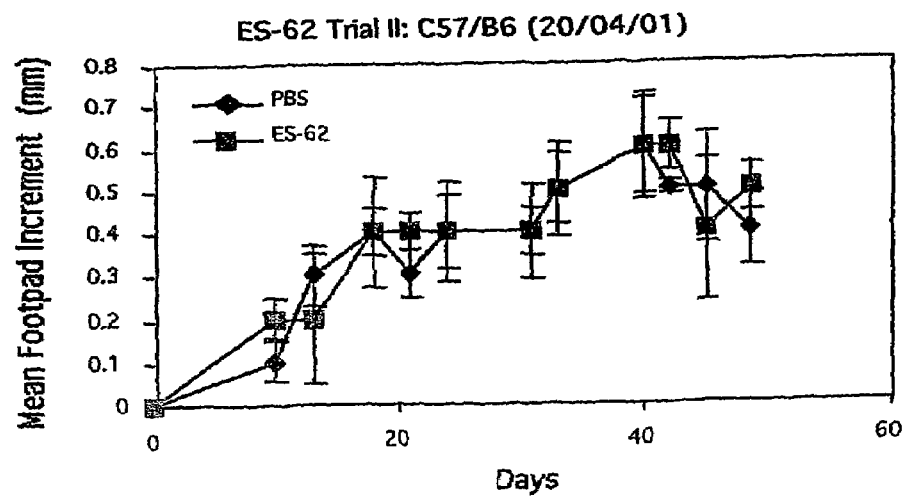
Figures 13A, 13B:
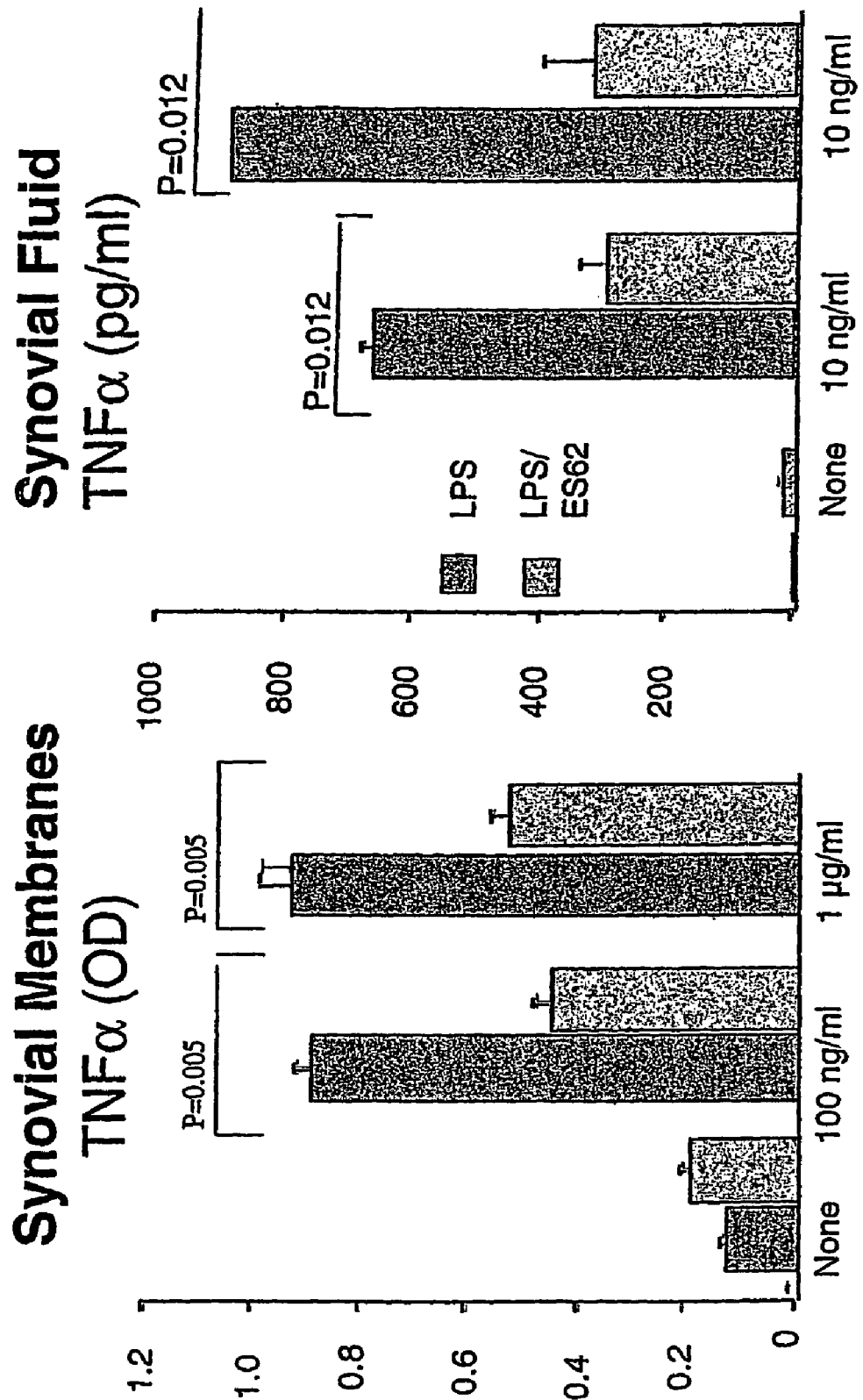

FIG. 12 shows that ES-62 treatment has no effect on footpad increment observed in Leishmania mouse strains. FIG.12A. Mean footpad incremement (mm) as a function of time in PBS and ES-62 treatment conditions in BALB/c mice. FIG. 12B. Mean footpad incremement (mm) as a function of time in PBS and ES-62 treatment conditions in C57/B6 mice (trial I). FIG. 12C. Mean footpad incremement (mm) as a function of time in PBS and ES-62 treatment conditions in C57/B6 mice (trial II). FIG. 13 shows that ES-62 inhibits pro-inflammatory cytokine production from human synovial membrane and fluid cells. FIG. 13A. TNFα release in single cell suspensions prepared from synovial membranes: 1) with no treatment; 2) treated with LPS at 100 ng/ml or 1 µg/ml for 24 hours; or 3) treated with ES-62 and LPS at 100 ng/ml or 1 µg/ml for 24 hours. FIG. 13B. TNFα release in single cell suspensions prepared from synovial membranes: 1) with no treatment; 2) treated with LPS at 10 ng/ml for 24 hours; or 3) treated with ES-62 and LPS at 10 ng/ml for 24 hours.

DETAILED DESCRIPTION

The present inventors have given particular attention to the ES-62 molecule, which is a glycoprotein with the unusual post-translation modification of phosphorylcholine attachment to an N-type glycan. They found this molecule to possess a plethora of immunomodulatory activities that can be classified under the umbrella of "anti-inflammatory". Thus, ES-62 reduces the ability of lymphocytes (both B- and T-) to proliferate in response to antigen, inhibits the ability of macrophages to produce pro-inflammatory cytokines such as IL-12, TNF-α and IL-6, modulates dendritic cell maturation to preferentially elicit TH-2-like responses, induces spleen cells to produce the anti-inflammatory cytokine, IL-10 and biases antibody responses in a TH-2/anti-inflammatory direction.

Figure 2:
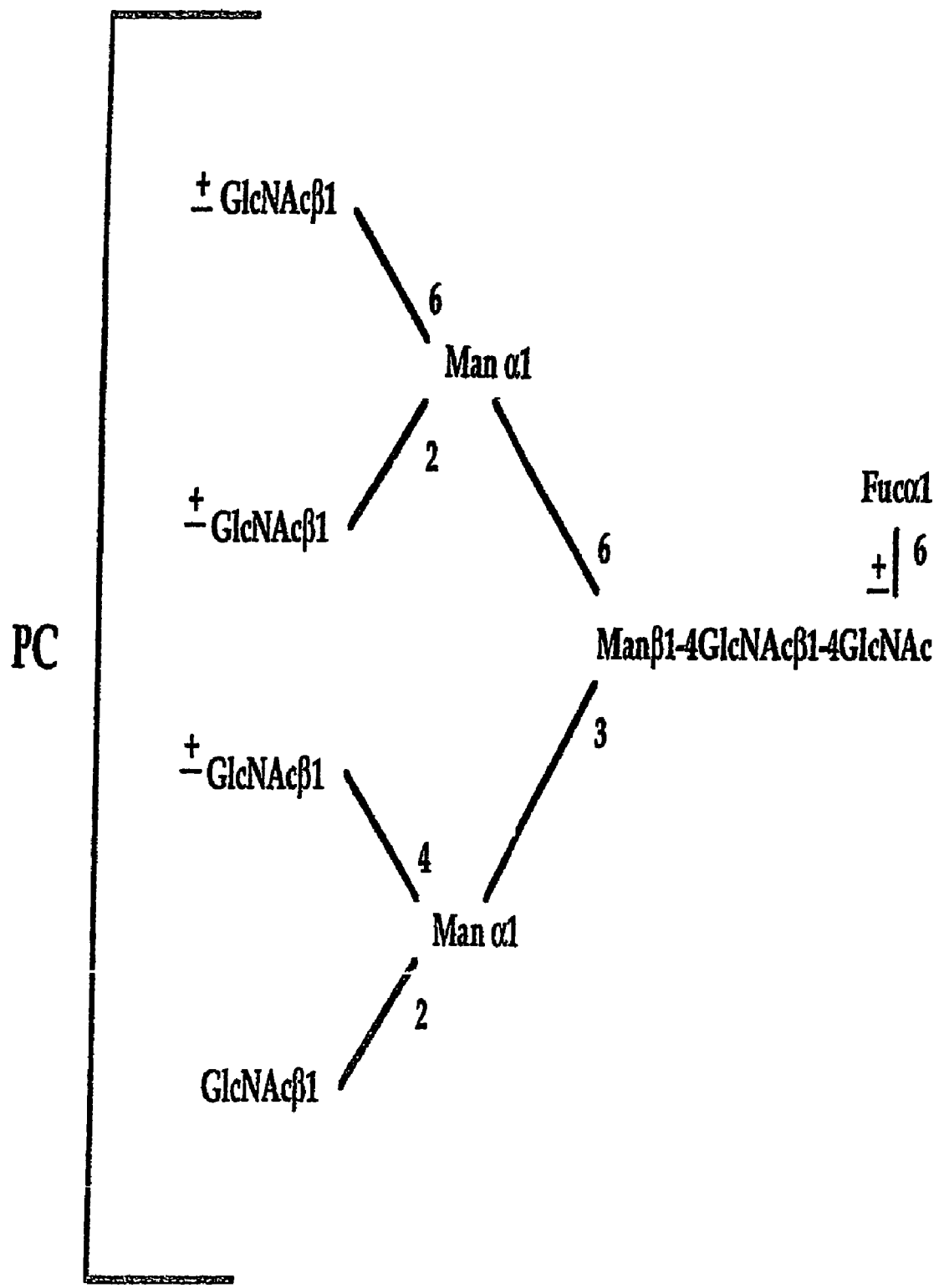
FIG. 2 shows the phosphorylcholine-glycan component structure of ES-62 (Haslam et al. (1997), Molecular and Biochemical Parasitology, 85,53). The numbers 2, 3, 4 and 6 refer to positions for the C-linkage. The + and − symbols merely mean that the units are optional.

ES-62 has been identified as a glycoprotein comprising the amino acid sequence shown in FIG. 1. The phosphorylcholine-glycan (PC-glycan) component of ES-62 is depicted as the structure shown in FIG. 2.

ES-62 may be prepared from spent culture medium from adult *A. viteae* maintained in RPMI complete at 37° C. in an atmosphere of 5% $CO_2$/95% air and was passed through filtration units with 0.22 µm membranes (Sigma) to remove microfilariae. The medium was concentrated to a volume of 10 ml/washed in PBS, pH 7.2, in a stirred cell with a PM10 membrane (Amicon, Upper Mill, UK). A further concentration step was undertaken using Centricon tubes (Amicon) with a 100-kDa membrane (ES-62 has a native m.w. of 280 kDa) to give a final volume of 0.5 ml. This was applied to a 30×1 cm Superose 6 column (HR 10/30, Pharmacia), fitted to an isocratic FPLC system (Pharmacia), previously equilibrated with PBS, pH 7.2, at room temperature. The column was eluted at a flow rate of 0.5 ml/mm and monitored for absorbance at 280 nm. The >95% of protein eluted as a single peak, which was confirmed to be ES-62 by analysis using SDS-PAGE. This was concentrated to 2 mg/ml and stored at −20° C. in 10-µl aliquots (Harnett, W. et al (1993) J. Immunol. 151. 4829).

Biochemical characterization of ES of adult *A. viteae* maintained in RPMI-1640 medium shows that it is dominated by one molecule, ES-62, so-called because it has a relative molecular mass of 62000 when analysed by SDS- PAGE under reducing conditions. It is estimated that ES-62 accounts for more than 95% of all of the protein released. ES-62 is also actively secreted by *A. viteae* in vivo, as shown by its detection in the bloodstream of parasitized jirds. ES-62 is of relevance to human filariasis because it shares considerable sequence homology with recently characterized EST's of *B. malayi* and because it contains phosphorylcholine, a molecule found on ES of all human filarial nematodes examined to date.

Investigation of the mechanism of attachment of PC to ES-62 revealed that it was via an N-type glycan (Harnett et al. (1993) Experimental Parasitology. 77, 498, Houston & Harnett (1996), Journal of Parasitology, 82, 320). Structural analysis of the PC-glycan of ES-62 indicated that at least 1–2 PC groups were present per glycan. Sequence analysis of ES-62 revealed that there were three potential N-linked glycosylation sites in the mature protein (Harnett et al. (1999), Molecular and Biochemical Parasitology, 104, 11). Thus, each molecule of ES-62 also reveals two leucine rich repeat regions: one of the properties of such motifs is that they promote protein dimerization and an estimation of the molecular mass of ES-62 by FPLC reveals a figure of approximately 280 000. Thus the native molecule appears to exist in a tetrameric form.

Inflammation is the hallmark of many diseases but the prototypical inflammatory diseases are the autoimmune diseases, which include type 1 diabetes melitus, rheumatoid arthritis, psoriasis, multiple sclerosis, autoimmune hepatitis, sarcoidosis and inflammatory bowel disease. Such chronic diseases are characteristically relapsing and remitting in nature and current treatment is inadequate.

For use according to the present invention, the glycoprotein ES-62 is preferably presented as a pharmaceutical formulation, comprising ES-62 or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersable granules, which may for example be suspended in water before administration, or sprinkled on food. The granules may be packaged, e.g., in a sachet.

Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release—controlling matrix, or is coated with a suitable release—controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles. Injectible preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics;

advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropnate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain ES-62 or a salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

EXPERIMENTAL

Materials, Methods and Results

Figure 3:
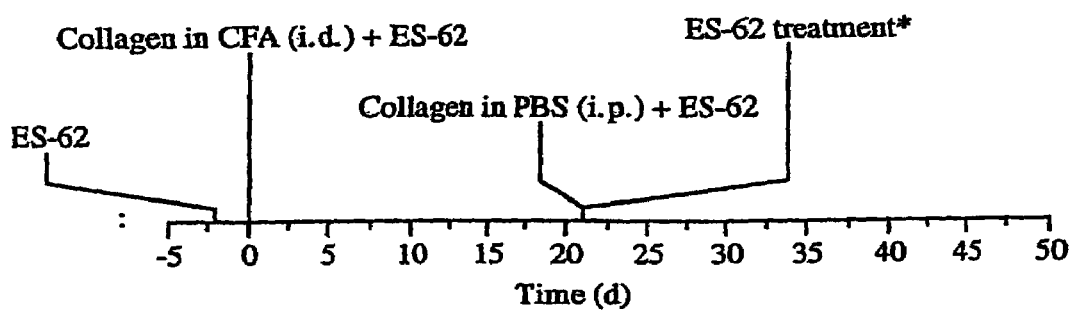
FIG. 3 shows a summary of the experimental protocol for collagen-induced arthritis.

Eight-ten week old mice (DBA/1 strain) were given 2 micrograms of purified ES-62 in 50 microliters phosphate-buffered saline (PBS) subcutaneously upon day −2, day 0 and day 21 (ES-62 group). A second group was additionally given ES-62 on days 22, 23 and 24 and every third day until the end of the study (ES-62 multi group) Control mice were simply given PBS (PBS group). All mice were also given 200 micrograms of collagen (bovine, type II; Sigma, Poole, Dorset) in 100 microliters Freunds complete adjuvant intradermally on day 0 and collagen in PBS intraperitoneally on day 21. A summary of the experimental protocol is shown in FIG. 3. In a separate therapeutic experiment performed after completion of the work just referred to, ES-62 (2 mg) was not given until 1 day after disease was established as being present and was then administered for fourteen consecutive days.

The incidence and severity of arthritis were measured daily up until day 50. Severity scores were derived as follows: 0=normal, 1=erythema, 2=erythema plus swelling, 3=extension/loss function, and total score=sum of four limbs. In the therapeutic study, measurements were undertaken during the 14 days in which ES-62 was administered.

Lymph node cells were recovered at day 33 and day 50 (one day after end of ES-62 administrations for therapeutic study) and proliferation and cytokine responses to collagen measured. Briefly cells were cultured at $2\times10^6$ cells/ml for up to 96 h in medium [RPMI (Gibco/BRL, Paisley, Glasgow U.K.), supplemented with 2 mM L-glutamine, 100 IU/ml penicillin, 100 mg/ml streptomycin, 25 mM HEPES buffer and 10% FCS (all Gibco/BRL)] at 37° C. in 5% $CO_2$. Cells were stimulated with graded concentrations of collagen. Proliferation assays were performed in triplicate in U-bottom 96-well plates (Nunc, Roskile, Denmark) as described previously (Leung, B. P. et. al. (2000) J. Immunol. 164, 6495). Supernatants from parallel triplicate cultures were stored at −70° C. until estimation of cytokine content by ELISA. Briefly, murine TNFα, IFNγ, (R&D Systems), IL-6, IL-10 and IL-12 (p40+p70) (PharMingen, San Diego, Calif.) were assayed by ELISA using paired antibodies according to the manufacturer's instructions. Lower limits of detection were as follows: IL-6, IL-12 and TNFα all at 10 pg/ml; IL-10 and IFNγ at 80 pg/ml.

Serum samples were recovered on day 50 (one day after end of ES-62 administrations for therapeutic study) and antibody responses to collagen measured by ELISA as described previously (Leung, B. P. et. al. (2000) J. Immunol. 164, 6495). Briefly, 96-well plates (Maxisorb, Nunc, Denmark) were coated with collagen (2 mg/ml in 0.1M $NaH_2CO_3$) overnight at 4° C., blocked and serial dilutions of sera were added. Bound IgG1/2a were detected with the aid of biotin-conjugated anti-mouse IgG1 or IgG2a (PharMingen) respectively.

Statistical analysis was performed using Minitab software for Macintosh. Clinical scores were analysed with the non-parametric Mann-Whitney U test. Differences between cumulative incidences at a given time point were analysed by the chi-square contingency analysis. Cytokine and collagen-specific IgG levels were compared using the Student's t-test.

On completion of the therapeutic study, mice had their hind paws removed and sections were prepared and stained with hematoxylin and eosin.

Balb/c or C57/B6 mice (groups of 5) were given 2 micrograms of purified ES-62 in 100 microliters PBS subcutaneously upon day −2, day 0 and day 2 (ES-62 group, Trial I). A second group of C57/B6 mice was additionally given ES-62 on days 4 and 6 (ES-62 group trial II) Control mice were simply given PBS (PBS group). All mice were also given $5 \times 10^6$ *Leishmania major* parasites in 50 μl PBS subcutaneously in one footpad. Parasite burden was assessed by the increment of footpad size (mm) in the infected footpad relative to paired uninfected footpad as described previously (Piedrafita D. et al. (1999) J Immunol 163:1467).

Figure 4A:
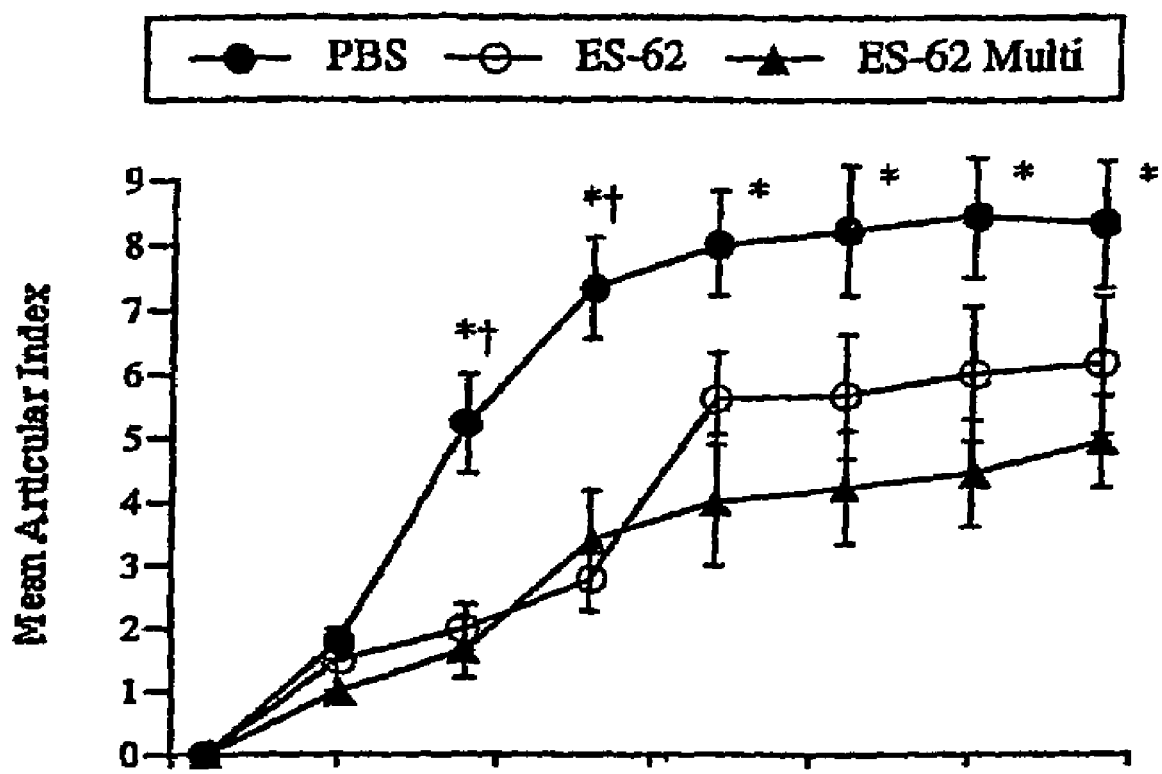
FIG. 4A. Mean articular index as a function of time.
Figure 4B:
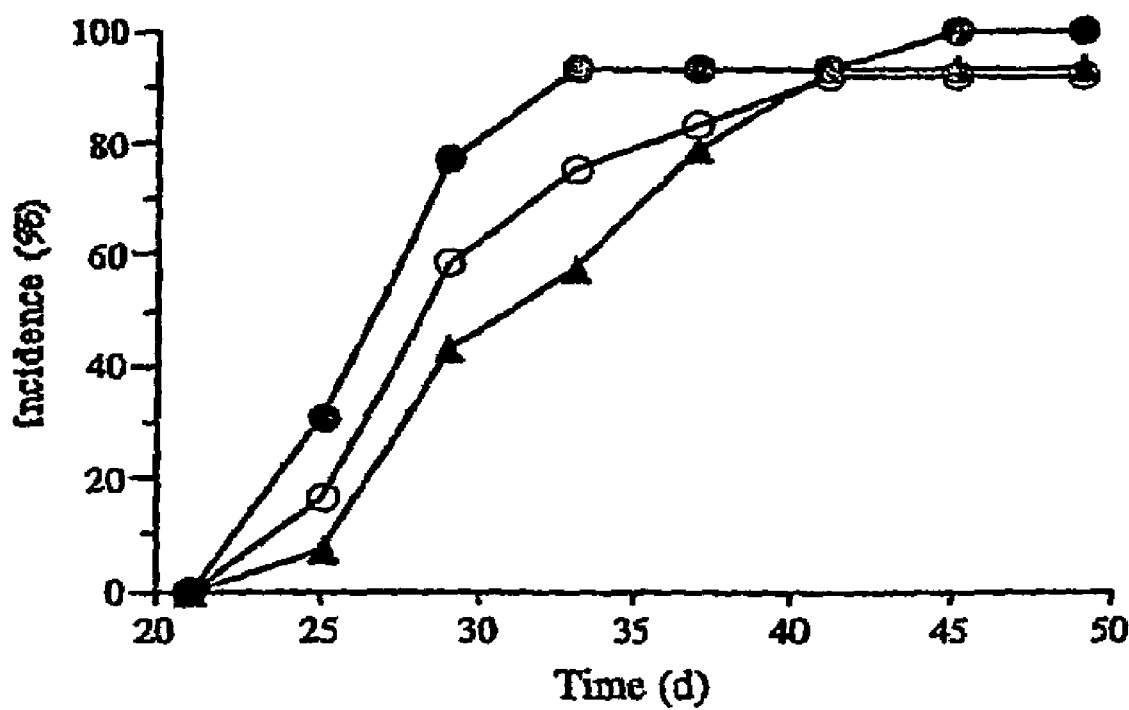
FIG. 4B. Incidence (%) of collagen-induced arthritis as a function of time. Data are expressed as mean +/−SEM.
Figure 5A:
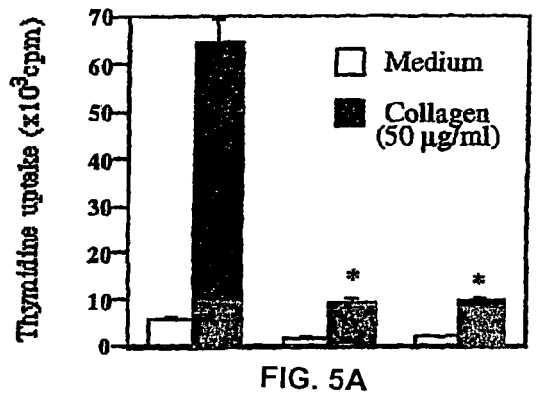
Figure 5B:
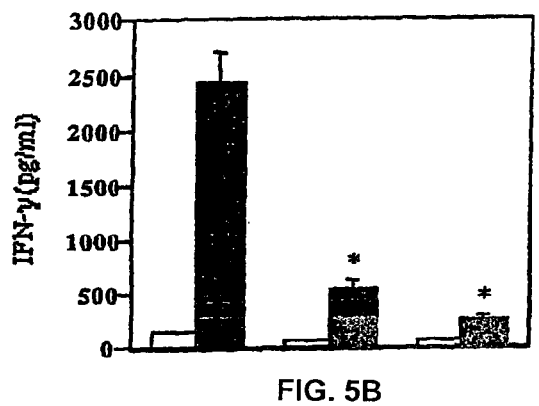
Figure 5C:
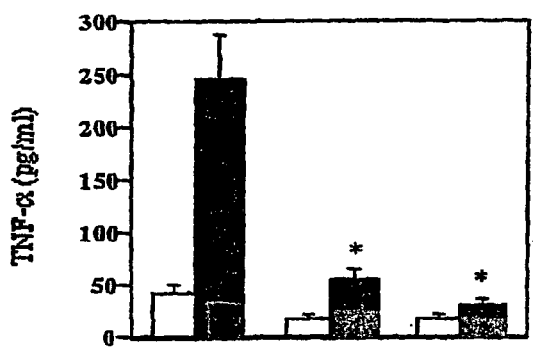
Figure 5D:
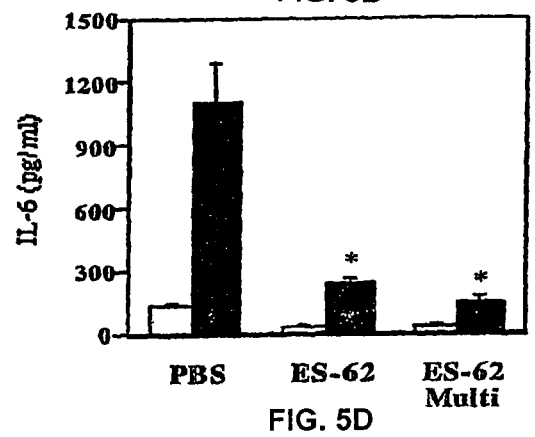
Figure 5E:
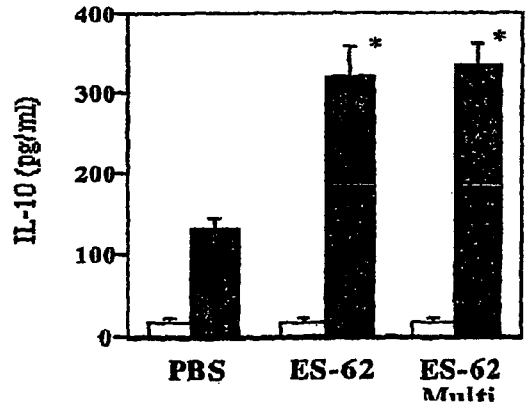
Figure 6A:
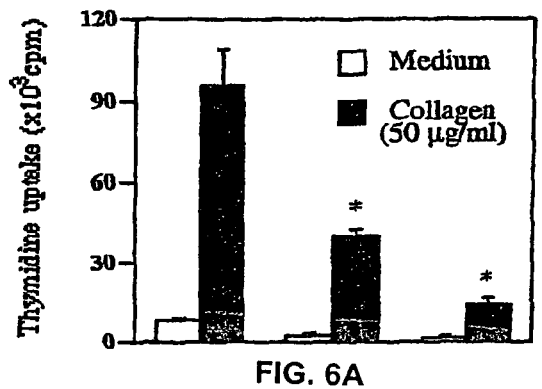
Figure 6B:
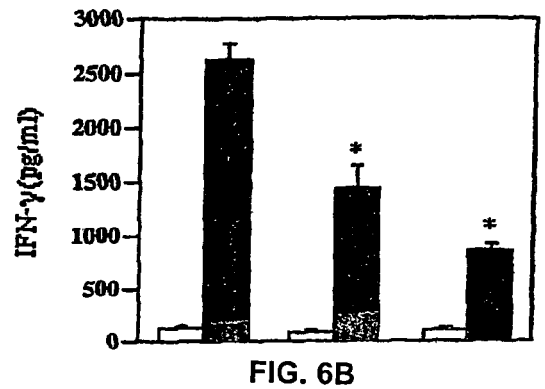
Figure 6C:
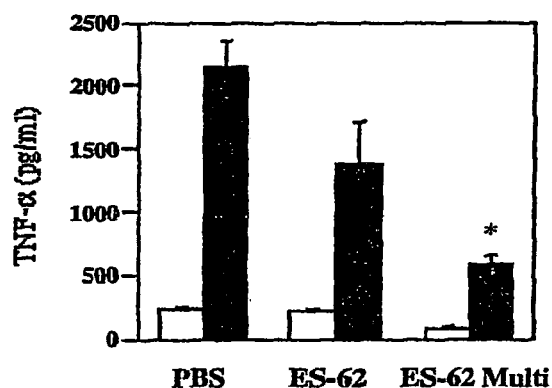
Figure 6D:
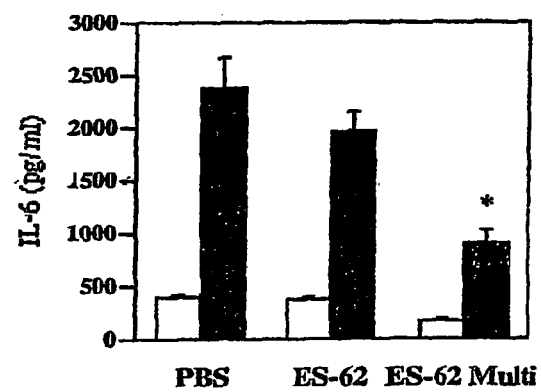

As shown in FIG. 4, the three-dose ES-62 protocol (ES-62 group) effectively reduced (statistically significant) the severity of developing arthritis (top panel). Initial studies indicate that the ES-62 multi treatment (ES-62 multi-group) may be more effective than the three dose ES-62 protocol (ES-62 group).

As shown in FIG. 5, the amelioration in severity of disease was matched ex vivo by suppression of antigen-induced cell proliferation in lymph node cultures at day 33. This effect was entirely specific: proliferative responses to the non-specific mitogen, Concanavalin A were not impaired.

As shown in FIG. 5, the amelioration in severity of disease was also matched ex vivo by suppression of production of the pro-inflammatory cytokines IL-6, TNFα and IFNγ in lymph node cultures at day 33.

Conversely as shown in FIG. 5, the production of the anti-inflammatory cytokine IL-10 was elevated.

As shown in FIG. 6, multi ES-62 treatment was effective in maintaining the inhibition of both cell proliferation and inflammatory cytokine production (day 50).

As shown in FIG. 7, production of the TH-1 antibody, IgG2a was reduced by the multi-treatment (day 50).

As shown in FIG. 8, therapeutic treatment with ES-62 after the onset of disease was effective in preventing progression of established arthritis in the murine collagen model.

As shown in FIG. 9, the prevention of further development of disease was matched ex vivo by suppression of antigen-induced cell proliferation in lymph node cultures prepared one-day after completion of 14 days of daily ES-62 administration.

As shown in FIG. 9, the prevention of further development of disease was also matched ex vivo by suppression of production of the pro-inflammatory cytokines IL-6, TNFα and IFNγ in lymph node cultures obtained one-day after completion of 14 days of daily ES-62 administration.

As shown in FIG. 10, production of the TH-1 antibody, IgG2a was reduced by the daily administration of ES-62 as detected one-day after completion of 14 days of daily ES-62 administration.

As shown in FIG. 11, treatment with ES-62 in the therapeutic study prevented the profound cartilage surface erosion and inflammation observed in mice which simply received PBS.

As shown in FIG. 12, treatment with ES-62 in the therapeutic study prevented the profound cartilage surface erosion and inflammation observed in mice which simply received PBS.

TNF production by synovial tissues is an important surrogate for pro-pathogenic pathways in vivo. FIG. 13 shows that ES-62 inhibits TNFα production from human tissues in vitro. Two single cell suspensions (i.e. A and B) prepared from RA synovial membrane or synovial fluid were pre-treated with ES-62 and subsequently stimulated with LPS (1000 ng/ml or 100 ng/ml) for 24 hours to optimize TNFα release in vitro. TNFα release into culture supernatants was measured by ELISA. Data are mean±SEM of triplicate cultures and are representative of three similar experiments.

FIG. 13 shows that ES-62 inhibits pro-inflammatory cytokine production from human synovial membrane and fluid cells.

CONCLUSIONS AND IMPLICATIONS

The data presented clearly indicate that the 3-dose ES-62 protocol significantly reduces severity of collagen-induced arthritis in mice. This reduction was associated with loss of the normal pro-inflammatory response to collagen and the development of an anti-inflammatory phenotype. This change was caused by a reversal in T-cell polarity—from TH-1 to TH-2 (as witnessed by changes in proliferation and cytokine production). Of additional interest, the effect on disease severity, and upon pro-inflammatory cytokine production ex vivo, was maintained by further administration of ES-62 given every three days. This strongly suggested that ES-62 has activity in suppressing ongoing arthritis. The results of the final experiment carried out—the therapeutic study, were entirely consistent with this. In this experiment, where mice were treated with ES-62 after the onset of pathology associated with collagen-induced arthritis, ES-62 prevented the further progression of disease. Hence ES-62 could be of value in the treatment of human arthritic disease. The presented data on effects of ES-62 on production of TNFα in human synovial cultures are consistent with this.

Finally, ES-62 may be a selective anti-inflammatory agent as it does not appear to modulate all diseases associated with polarisation of the T helper phenotype. For example, in mice, susceptibility to infection with *Leishmania* is associated with a TH2 phenotype (Balb/c) whereas resistance and clearance of parasite is associated with a TH1 phenotype. Indeed, disease is exacerbated in mice deficient in pro-inflammatory cytokines such as IL-12 and TNF-alpha. Thus if ES-62 were to mediate its effects simply by being "anti-inflammatory" or reversing TH1 polarity, it would be expected to exacerbate disease in Balb/c (TH2) mice and render C57/B6 (TH1) mice susceptible to infection. In contrast, treatment with ES-62 had no effect on either strain of mouse.

The invention claimed is:

1. A method of treating an inflammatory disease in an animal in need thereof comprising administering to said animal a therapeutically effective amount of ES-62, wherein the inflammatory disease is selected from the group consisting of arthritis and chronic obstructive pulmonary disease.

2. The method of claim 1, wherein the disease is arthritis.

3. The method of claim 1, wherein the disease is rheumatoid arthritis.

* * * * *

UNITED STATES PATENT AND TRADEMARK OFFICE
CERTIFICATE OF CORRECTION

| | | |
|---|---|---|
| PATENT NO. | : 7,067,480 B2 | Page 1 of 1 |
| APPLICATION NO. | : 10/490197 | |
| DATED | : June 27, 2006 | |
| INVENTOR(S) | : Harnett et al. | |

It is certified that error appears in the above-identified patent and that said Letters Patent is hereby corrected as shown below:

<u>Column 3</u>:

Line 29, "IG2a" should read --IgG2a--;

Line 37, "proaression" should read --progression--.

Signed and Sealed this

Seventeenth Day of October, 2006

JON W. DUDAS
*Director of the United States Patent and Trademark Office*

SEQUENCE LISTING

<160> NUMBER OF SEQ ID NOS: 1

<210> SEQ ID NO 1
<211> LENGTH: 474
<212> TYPE: PRT

<213> ORGANISM: Acanthocheilonema viteae

<400> SEQUENCE: 1

```
Ala Ala Val Leu Pro Asp Lys Thr Val Ala Pro Lys Asn Tyr Ile Gln
  1               5                  10                  15
Glu Thr Phe Gly Lys Glu Val Ala Glu Leu Ile Gln Tyr Ile Thr Lys
             20                  25                  30
Gly Glu Glu Val Gly Leu Ala Tyr Gln Trp Leu Ser Lys Leu Val Asp
         35                  40                  45
Gly Phe Gly His Arg Met Val Gly Ser Asp Ser Leu Glu Lys Ser Ile
     50                  55                  60
Ala Phe Leu Glu Glu Ser Leu Lys Asn Asp Asn Phe Asp Lys Val His
 65                  70                  75                  80
Thr Glu Glu Val Pro Asn Leu Pro His Trp Val Arg Gly Asn Asp Val
                 85                  90                  95
Val Glu Met Ile Glu Pro Arg Asn Gln Arg Leu Asn Val Leu Ala Ile
            100                 105                 110
Gly Gly Ser Glu Pro Ala Ser Ala Thr Gly Glu Val Thr Val Ile Tyr
        115                 120                 125
Asp Leu Asp Asp Val Lys Pro Asp Val Arg Gly Lys Ile Val Val
    130                 135                 140
Thr Ala Gln Thr Phe Ala Gly Tyr Pro Leu Thr Leu Lys Tyr Arg Arg
145                 150                 155                 160
Ser Val Lys Leu Phe Glu Gln Leu Gly Ala Ile Gly Val Leu Val Lys
                165                 170                 175
Ser Ile Thr Ser Phe Ser Ile Asn Ser Pro His Thr Gly Thr Gly Ala
            180                 185                 190
Glu Asn Thr Thr Ile Pro Ala Ala Cys Leu Thr Ile Glu Glu Ala Glu
        195                 200                 205
Met Leu Glu Arg Leu Tyr Arg Ser Gly Lys Lys Ile Val Ile Arg Met
    210                 215                 220
Asp Met Lys Ser His Tyr Glu Glu Pro Ile Asn Ser Ser Asn Leu Ile
225                 230                 235                 240
Phe Glu Ile Thr Gly Ser Glu Arg Pro Ser Glu Val Val Leu Leu Ser
                245                 250                 255
Ala His Val Asp Ser Trp Asp Val Gly Gln Gly Ala Leu Asp Asp Gly
            260                 265                 270
Ala Gly Cys Ala Val Val Trp Ser Ala Leu His Ser Leu Lys Lys Leu
        275                 280                 285
Ala Glu Arg Asn Pro Lys Phe Lys Pro Lys Arg Thr Ile Arg Gly Ile
    290                 295                 300
Phe Trp Thr Ser Glu Glu Gln Gly Tyr Gly Gly Ala Lys His Tyr Tyr
305                 310                 315                 320
Ile Thr His Lys Asn Asp Ser Pro Glu Lys Phe Tyr Phe Val Ser Glu
                325                 330                 335
Thr Asp Thr Gly Thr Phe Lys Ser Thr Asn Trp Leu Ala His Leu Ser
            340                 345                 350
Phe Ser Gly Asp Lys Lys Ser Met Leu Arg Leu Lys Glu Ile Thr Arg
        355                 360                 365
Leu Leu Ser Arg Asn Gly Ile Ala Leu Gly Leu Ile Asn Ser Ser Val
    370                 375                 380
Gln Gly Asp Val Thr Phe Trp Ala Lys Asp Gly Ile Pro Ser Val Asn
385                 390                 395                 400
```

-continued

```
Tyr Ile Pro Asp Lys Ala Val Asp Tyr Tyr Phe Tyr Phe His His Thr
            405                 410                 415

Ala Gly Asp Tyr Met Thr Val Leu Lys Asp Gly Asp Leu Glu Tyr Thr
            420                 425                 430

Thr Ser Ile Phe Ala Thr Leu Gly His Val Ile Ala Asn Met Asp Asp
            435                 440                 445

Trp Gly Ser Asp Pro Asn Gln Pro Gln Gln Leu Asn Ser Lys Gln Ser
    450                 455                 460

Thr Thr Glu Lys Ser Asp Arg Lys Lys Leu
465             470
```